United States Patent [19]

Von Werner

[11] Patent Number: 5,639,923
[45] Date of Patent: Jun. 17, 1997

[54] METAL-CATALYZED PREPARATION OF PERFLUOROALKYL IODIDE TELOMERS

[75] Inventor: Konrad Von Werner, Garching, Germany

[73] Assignee: Hoechst Aktiengesellschaft, Frankfurt, Germany

[21] Appl. No.: 575,992

[22] Filed: Dec. 21, 1995

[30] Foreign Application Priority Data

Dec. 24, 1994 [DE] Germany .......................... 44 46 758.3

[51] Int. Cl.$^6$ .................. C07C 17/278; C07C 19/07; C07C 19/16; C07C 17/269
[52] U.S. Cl. .................................. 570/139; 570/172
[58] Field of Search ........................... 570/139, 172

[56] References Cited

U.S. PATENT DOCUMENTS

| | | | |
|---|---|---|---|
| 3,557,224 | 1/1971 | Jaeger | 570/139 |
| 3,883,604 | 5/1975 | Rudolph et al. | 570/139 |
| 4,587,366 | 5/1986 | von Werner | 570/172 |

FOREIGN PATENT DOCUMENTS 140254  5/1986  European Pat. Off. .

OTHER PUBLICATIONS

Chen, Q-Y, et al, *J. of Fluorine Chem.* 36:483–489 (1987).

*Primary Examiner*—Joseph E. Evans
*Attorney, Agent, or Firm*—Connolly and Hutz

[57] ABSTRACT

The selectivity of copper as the catalyst for the reaction of short-chain perfluoroalkyl iodides with tetrafluoroethylene is increased if a further transition metal is employed as a cocatalyst.

16 Claims, No Drawings

METAL-CATALYZED PREPARATION OF PERFLUOROALKYL IODIDE TELOMERS

CROSS-REFERENCE TO RELATED APPLICATION

This application is related to the copending application of Konrad Von Werner, entitled "Process for the preparation of perfluoroalkyl iodide telomers", filed of even date herewith Ser. No. 08/576,648, the disclosure of which is hereby incorporated by reference.

DESCRIPTION

Medium- to longer-chain perfluoroalkyl iodides are starting materials for the preparation of fluorinated surfactants and of hydro- and oleophobizing treatment materials, for example for textiles. On the other hand, n-perfluorooctyl iodide in particular is a starting material for n-perfluorooctyl bromide, which has acquired considerable importance in the medical sector.

Perfluoroalkyl iodides are prepared industrially by telomerization in accordance with the equation

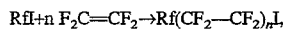
$$RfI + n\, F_2C=CF_2 \rightarrow Rf(CF_2-CF_2)_nI,$$

in which Rf is perfluoroalkyl having 1 to 6 carbon atoms and n is a number from 1 to about 8. The reaction is started either by heating (for example U.S. Pat. No. 5,268,516) or by agents which form free radicals (for example GB-A 1 535 408 or U.S. Pat. No. 5,068,471). Perfluoroalkanes are formed to a considerable extent in the thermal reaction by dimerization of the perfluoroalkyl radicals intermediately formed, and hydrogen-containing compounds occur as by-products in the free radical reactions.

As can be seen from the abovementioned reaction equation, the formation of the generally undesirable longer-chain telomers is suppressed by a high concentration of the telogen RfI. Selectivity in the direction of the desired medium-chain telomers is therefore at the expense of high conversions, with which a high expenditure on distillation of telogen to be recycled and short-chain telomers are associated.

In a publication called a "Preliminary Note", Chen et al., Journal of Fluorine Chemistry 36 (1987), pages 483 to 489, describe the use of copper as a telomerization catalyst. This process has the advantage that the reaction already proceeds at 80° to 100° C. and requires shorter reaction times in relation to high-temperature telomerizations. Relatively large amounts of undesirable longer-chain telomers are still formed in the reaction of perfluoroethyl iodide and tetrafluoroethylene in a molar ratio of 1:2 to 2:1.

Surprisingly, it has now been found that the selectivity of copper as catalyst for the telomerization reaction can be increased in the direction of the medium-chain products desired if the copper is employed in combination with a further transition metal. Thus, the invention relates to a process for the preparation of a perfluoroalkyl iodide telomer of the formula

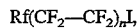
$$Rf(CF_2-CF_2)_nI,$$

in which Rf is perfluoroalkyl having 1 to 6 carbon atoms and n is a number from 1 to about 4, the maximum number of carbon atoms in the resulting telomer mixture being in the range from 6 to 10, which comprises reacting a perfluoroalkyl iodide of the formula RfI, in which Rf has the abovementioned meaning, with tetrafluoroethylene with a catalyst comprising copper and a further transition metal as a cocatalyst.

The said further transition metal includes those which in themselves do not catalyze the reaction or catalyze it only weakly, such as iron, cobalt, nickel, chromium, molybdenum, tungsten or titanium. It is of course also possible for more than one of these weakly active or inactive metals to be employed in combination with the copper. When the "other" metal is thus referred to for simplicity below, the intention is not to exclude more than one weakly active or inactive metal being used in addition to the copper. It is furthermore also possible to employ another catalytically active metal, such as zinc, manganese, vanadium, rhodium or silver, in addition to the copper.

The copper can be employed in finely divided form as a mixture with the other metal, or as a coating of the other metal. This can in turn be fixed to a support of high surface area. The customary catalyst supports, such as aluminum oxide, kieselguhr or molecular sieves, are suitable for this.

If the reaction is carried out in an autoclave, the reaction space of which is made of one of the metals of low activity, such as steel or nickel, or is lined with these metals, these materials can be provided with a thin copper coating.

Preferred telogens are 2-iodoperfluoropropane, and 1-iodoperfluoroethane, -butane and -hexane. It has been found that the rate of reaction when 1-iodoperfluorobutane and -hexane are employed is about 1.6 times higher than with 1-iodoperfluoroethane. A preferred embodiment of the invention thus comprises employing these lower telomers as telogens—in the pure form or as mixtures.

Since the reaction according to the invention is multi-phase—the gas tetrafluoroethylene is reacted with the liquid telogen over a solid catalyst—good thorough mixing is to be ensured. Supported catalysts in which the metal combinations are applied to a support of relatively low density are therefore advantageous, since the floatability in the liquid perfluoroalkyl iodide phase is improved in this way. The use of a stirrer through which the tetrafluoroethylene is gassed into the liquid phase is furthermore advantageous. So-called jet reactors in which the liquid phase is pumped in circulation via a nozzle together with the catalyst are also favorable. The gas—in this case tetrafluoroethylene—is metered in shortly before the nozzle. The high shearing forces generated in the nozzle cause effective gas/liquid transition. These reactors are also suitable for continuous operation.

It has furthermore been found that water—if oxygen is excluded—does not lead to an increased formation of by-products and also impairs the reaction only little. It is thus not necessary to dry the starting materials.

Further preferred embodiments of the invention can be seen from the following examples.

EXAMPLES

The results were evaluated by gas chromatography, direct evaluation of the data found in the form of parts by weight being obtained by means of experimentally calibrated area factors.

Before use, the perfluoroalkyl iodides employed were freed from impurities such as hydrogen fluoride or iodine with potassium carbonate powder and were stored under nitrogen. Purity determined by gas chromatography:

| | |
|---|---|
| $F_2C=CF_2$ | 99.98% |
| n-$C_2F_5I$ | 97.5% |
| n-$C_4F_9I$ | 99.8% |
| n-$C_6F_{13}I$ | 98.7% |
| i-$C_3F_7I$ | 99.5% |

Examples 1 to 12

The reactions were carried out in a 300 ml shaking autoclave of high-grade steel ($V_4A$, material 1.4571). The stated amount of catalyst was initially introduced into the autoclave under nitrogen. After a pressure trial with 50 bar of nitrogen, the autoclave was evacuated to 1 mbar and then cooled to −78° C. After the stated amount of perfluoroalkyl iodide had been sucked in, the desired amount of tetrafluoroethylene ("TFE" in the tables) was condensed in at −78° C. (weighing must be performed rapidly in order to avoid errors due to icing up of the autoclave).

Examples 1 to 3 and Comparison Examples V1 and V2

69.2 g of 1-iodo-n-perfluorobutane were shaken in the stated molar ratio with tetrafluoroethylene with the stated amount of catalyst at 100° C. for 5 hours. The results are shown in Table 1. The sum of all the non-RfI compounds is totaled in the last column under "Σ X". In the evaluation by gas chromatography, these compounds were weighted globally with the weight factor 1.00. They are, for example, tetrafluoroethylene, RfH compounds (which are contained in the starting materials in a small amount), perfluoroalkanes and water (which was introduced into the system during metering of the samples with a cooled syringe).

A nickel powder doped with 0.25% by weight of copper was employed in Examples 2 and 3.

In Example 3—in contrast to Example 2—the tetrafluoroethylene was metered into the autoclave in two portions.

250° C. During this operation, the pressure was released several times and hydrogen was forced in again, in order to remove acetic acid and residual water. The activated catalyst was stored under nitrogen. It comprises 73.5% mg of nickel and 8.0 mg of copper per gram. In each case 5 g of catalyst, i.e. corresponding to 367.5 mg of copper (5.78 mmol) and 40.0 mg of nickel (0.68 mmol), were employed for the examples. In each case 69.2 g (0.2 mol) of 1-iodo-perfluorobutane were employed. The results are shown in Table 2.

TABLE 1

| Ex. | Catalyst | [g] | [mmol] | Molar ratio $C_4F_9I/TFE$ | Product distribution $C_2F_5(CF_2-CF_2)_n$-I [% by weight], n = | | | | | | | | | | |
|---|---|---|---|---|---|---|---|---|---|---|---|---|---|---|---|
| | | | | | 1 | 2 | 3 | 4 | 5 | 6 | 7 | 8 | 9 | 10 | Σ X |
| V1 | Cu | 2.0 | 31.5 | 1.82 | 54.5 | 25.2 | 11.1 | 4.7 | 1.9 | 0.8 | 0.4 | 0.2 | 0.1 | <0.1 | 1.1 |
| V2 | Ni | 2.0 | 34.1 | 2.0 | No reaction | | | | | | | | | | |
| 1 | Ni + Cu | 2.0 0.05 | 34.1 0.8 | 2.0 | 58.0 | 23.2 | 9.6 | 4.9 | 2.2 | 0.8 | 0.4 | 0.2 | 0.1 | — | 0.6 |
| 2 | Ni + Cu | 2.0 0.05 | 34.1 0.8 | 1.82 | 49.6 | 26.0 | 12.9 | 5.9 | 2.7 | 1.1 | 0.5 | 0.2 | 0.1 | <0.1 | 1.2 |
| 3 | Ni + Cu | 2.0 0.05 | 34.1 0.8 | 1.82 | 58.6 | 25.2 | 9.4 | 3.3 | 1.1 | 0.4 | 0.2 | 0.1 | — | — | 1.8 |

Examples 4 to 11

The reaction was carried out analogously to the preceding examples, but with the following catalysts:

TABLE 2

| Ex. | Support | Molar ratio $C_4F_9I/TFE$ | Product distribution $C_2F_5(CF_2-CF_2)_n$-I (% by weight), n = | | | | | | | | | |
|---|---|---|---|---|---|---|---|---|---|---|---|---|
| | | | 1 | 2 | 3 | 4 | 5 | 6 | 7 | 8 | 9 | Σ X |
| 4 | Zeolite (10 Å)/1st use | 2.0 | 48.5 | 30.6 | 12.9 | 4.8 | 1.6 | 0.6 | 0.2 | 0.1 | <0.1 | 0.6 |
| 5 | Zeolite (10 Å)/2nd use | 1.82 | 39.3 | 32.7 | 16.1 | 6.9 | 2.7 | 1.1 | 0.5 | 0.2 | 0.1 | 0.4 |
| 6 | Zeolite (10 Å)/3rd use | 2.0 | 56.2 | 23.7 | 10.8 | 5.1 | 2.2 | 0.9 | 0.4 | 0.2 | 0.1 | 0.4 |
| 7 | Zeolite (10 Å)/4th use | 2.0 | 65.1 | 18.8 | 8.2 | 4.1 | 1.9 | 0.8 | 0.4 | 0.2 | 0.1 | 0.4 |
| 8 | Zeolite (3 Å) | 2.0 | 52.6 | 25.1 | 11.2 | 5.6 | 2.8 | 1.2 | 0.5 | 0.2 | 0.1 | 0.7 |
| 9 | $Al_2O_3$ | 2.0 | 57.4 | 22.9 | 9.7 | 5.2 | 2.4 | 1.0 | 0.5 | 0.2 | 0.1 | 0.6 |
| 10 | Kieselguhr | 2.0 | 56.0 | 26.3 | 10.4 | 4.0 | 1.5 | 0.5 | 0.2 | 0.1 | — | 1.0 |
| 11 | — | 2.0 | 75.0 | 14.2 | 5.0 | 2.1 | 0.9 | 0.5 | 0.3 | 0.2 | 0.1 | 1.6 |

34 mmol of nickel(II) acetate and 3.4 mmol of copper(II) acetate were dissolved in 150 ml of desalinated water. The solution was concentrated to about 80 ml and stirred with the support material stated in Table 2. The mixture was then dehydrated under 15 mbar at 190° C. and the catalyst was activated by hydrogenation under 180 bar of hydrogen at Example 12 and Comparison Examples V3 and V4

Example 12 was carried out analogously to Examples 1 to 3.

In contrast, Comparison Examples V3 and V4 were carried out with 50 g of perfluoroethyl iodide. The results are shown in Table 3.

TABLE 3

| Example | Catalyst | [g] | [mmol] | Molar ratio RfI/TFE | Product distribution $C_2F_5(CF_2-CF_2)_n-I$ [% by weight], n = | | | | | | | | | |
|---|---|---|---|---|---|---|---|---|---|---|---|---|---|---|
| | | | | | 0 | 1 | 2 | 3 | 4 | 5 | 6 | 7 | 8 | ΣX |
| V3 | Cu | 2.0 | 31.5 | 2.22 | 63.4 | 11.9 | 7.2 | 5.3 | 3.9 | 2.9 | 1.9 | 1.0 | 0.4 | 2.1 |
| V4 | Fe | 2.0 | 35.8 | 4.0 | 97.2 | 0.1 | | | | | | | | 2.7 |
| 12 | Fe + | 2.0 | 35.8 | 2.0 | — | 58.7 | 24.8 | 9.8 | 4.2 | 1.5 | 0.6 | 0.2 | 0.1 | 0.1 |
|    | Cu   | 0.05 | 0.8 | | | | | | | | | | | |

Example 13 and Comparison Example V4

89.5 g of 1-iodo-n-perfluorohexane were reacted at 100° C. analogously to the preceding examples. The results are shown in Table 4.

Comparison Example V2 shows the inactivity of nickel (Table 1).

TABLE 4

| Ex. | Catalyst | [g] | [mmol] | Molar ratio $C_6F_{13}I/TFE$ | Product distribution $C_2F_5(CF_2-CF_2)_n-I$ [% by weight], n = | | | | | | | | |
|---|---|---|---|---|---|---|---|---|---|---|---|---|---|
| | | | | | 2 | 3 | 4 | 5 | 6 | 7 | 8 | 9 | ΣX |
| V4 | Cu | 2.0 | 31.5 | 2.0 | 53.0 | 24.5 | 9.8 | 3.6 | 1.3 | 0.5 | 0.2 | 0.1 | 6.5 |
| 13 | Ni + | 2.0 | 34.1 | 2.0 | 56.1 | 24.4 | 8.7 | 2.9 | 0.9 | 0.3 | 0.1 | — | 5.8 |
|    | Cu   | 0.1 | 1.6 | | | | | | | | | | |

Examples 14 and Comparison Example V5

In Example 14 1200 g and in Comparison Example V5 865 g of 1-iodo-n-perfluorobutane were reacted in each case in a molar ratio of 2:1 with tetrafluoroethylene in a 1 l stirred tank at 90° C. in the course of 2.5 hours. The stirred tank was equipped with a sheath for the thermocouple and a gassing stirrer, the tetrafluoroethylene being fed in through the hollow stirrer shaft and swirled into the liquid phase in the form of fine bubbles via fine bores at the end of the stirrer blades. The gassing stirrer had a maximum speed of 500 rpm. The results are shown in Table 5.

TABLE 5

| Example | Catalyst | [g] | [mmol] | $n_1$ [g] | Product distribution $C_2F_5(CF_2-CF_2)_n-I$ [% by weight], n = | | | | | | | |
|---|---|---|---|---|---|---|---|---|---|---|---|---|
| | | | | | 1 | 2 | 3 | 4 | 5 | 6 | 7 | ΣX |
| V5 | Zn | 15.0 | 229.4 | 865 | 51.1 | 28.5 | 12.5 | 4.4 | 1.3 | 0.3 | 0.1 | 1.8 |
| 14 | Zn + | 15.0 | 229.4 | 1200 | 50.3 | 29.1 | 13.2 | 4.4 | 1.3 | 0.3 | 0.1 | 1.3 |
|    | Cu   | 0.5 | 7.9 | | | | | | | | | |

TABLE 6

| Ex. | Product distribution $(CF_3)_2CF(CF_2-CF_2)_n-I$ [% by weight], n = | | | | | | | | | | |
|---|---|---|---|---|---|---|---|---|---|---|---|
| | 0 | 1 | 2 | 3 | 4 | 5 | 6 | 7 | 8 | 9 | ΣX |
| 15 | 60.5 | 15.3 | 9.0 | 5.9 | 3.3 | 1.8 | 0.9 | 0.5 | 0.2 | 0.1 | 2.5 |

Example 15

29.6 g (0.1 mol) of perfluoroisopropyl iodide were reacted with 5.0 g (0.05 mmol) of tetrafluoroethylene at 100° C. in the presence of 1.0 g (17.0 mmol) of nickel and 0.05 g (0.8 mmol) of copper in the autoclave mentioned for Examples 1 to 12 in the course of 5 hours. The results are shown in Table 6.

I claim:

1. A process maximizing the preparation of a perfluoroalkyliodide telomer of the formula

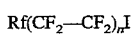

$$Rf(CF_2-CF_2)_nI$$

in essentially pure form or in a mixture, in which Rf is perfluoroalkyl having 1 to 6 carbon atoms and n is a number from 1 to about 4, the maximum number of carbon atoms of said telomer in the case in which Rf has 1 to 4 carbon atoms, being in the range from 6 to 10, and the maximum number of carbon atoms of said telomer, in the case in which Rf is more than 4 carbon atoms, being in the range of 8 to 10, which comprises reacting a perfluoroalkyl iodide of the formula RfI, in which Rf has the abovementioned meaning, with tetrafluoroethylene with a catalyst comprising copper metal and a further transition metal as a cocatalyst.

2. The process as claimed in claim 1, wherein the metal employed as a cocatalyst is in itself catalytically inactive or only weakly catalytically active.

3. The process as claimed in claim 2, wherein a metal which is in itself only weakly active or inactive is coated with copper.

4. The process as claimed in claim 1, wherein the cocatalyst is selected from the group consisting of zinc, manganese, vanadium, rhodium and silver.

5. The process as claimed in claim 1, wherein the metals are fixed to a support.

6. The process as claimed in claim 2, wherein the metals are fixed to a support.

7. The process as claimed in claim 4, wherein the metals are fixed to a support.

8. The process as claimed in claim 1, wherein the tetrafluoroethylene is gassed into the liquid phase with a stirrer.

9. The process as claimed in claim 2, wherein the tetrafluoroethylene is gassed into the liquid phase with a stirrer.

10. The process as claimed in claim 3, wherein the tetrafluoroethylene is gassed into the liquid phase with a stirrer.

11. The process as claimed in claim 4, wherein the tetrafluoroethylene is gassed into the liquid phase with a stirrer.

12. The process as claimed in claim 5, wherein the tetrafluoroethylene is gassed into the liquid phase with a stirrer.

13. The process as claimed in claim 6, wherein the tetrafluoroethylene is gassed into the liquid phase with a stirrer.

14. The process as claimed in claim 7, wherein the tetrafluoroethylene is gassed into the liquid phase with a stirrer.

15. The process as claimed in claim 8, wherein the tetrafluoroethylene is gassed into the liquid phase with a stirrer.

16. The process as claimed in claim 1, wherein said telomer is a mixture in which the average number of carbon atoms in said telomer is in the range of 6 to 10.

* * * * *